US012458395B2

(12) United States Patent
Ozawa et al.

(10) Patent No.: US 12,458,395 B2
(45) Date of Patent: Nov. 4, 2025

(54) LACRIMAL SAC INCISION KNIFE

(71) Applicant: KAI R&D CENTER CO., LTD., Gifu (JP)

(72) Inventors: Naoki Ozawa, Gifu (JP); Kazuyuki Hasebe, Gifu (JP); Kazuhiko Isogimi, Gifu (JP); Shinya Sonoda, Kagoshima (JP)

(73) Assignee: KAI R&D CENTER CO., LTD., Gifu (JP)

( * ) Notice: Subject to any disclaimer, the term of this patent is extended or adjusted under 35 U.S.C. 154(b) by 285 days.

(21) Appl. No.: 18/027,142

(22) PCT Filed: Apr. 7, 2021

(86) PCT No.: PCT/JP2021/014807
§ 371 (c)(1),
(2) Date: Mar. 20, 2023

(87) PCT Pub. No.: WO2022/079935
PCT Pub. Date: Apr. 21, 2022

(65) Prior Publication Data

US 2023/0329747 A1 Oct. 19, 2023

(30) Foreign Application Priority Data

Oct. 13, 2020 (JP) ................................ 2020-172726

(51) Int. Cl.
*A61B 17/3211* (2006.01)

(52) U.S. Cl.
CPC ................................ *A61B 17/3211* (2013.01)

(58) Field of Classification Search
CPC ..... A61B 17/3211; A61B 17/32; A61B 17/24; A61B 17/320016; A61F 9/00772
See application file for complete search history.

(56) References Cited

U.S. PATENT DOCUMENTS 5,217,477 A * 6/1993 Lager ................ A61B 17/3211 606/166
5,258,002 A * 11/1993 Jeffers .................. A61F 9/0133 30/348

(Continued)

FOREIGN PATENT DOCUMENTS

CN 201617915 U 11/2010
CN 203749507 U 8/2014

(Continued)

OTHER PUBLICATIONS

International Search Report corresponding to International Application No. PCT/JP2021/014807 mailed Jun. 22, 2021, in English.

(Continued)

*Primary Examiner* — Anh T Dang
(74) *Attorney, Agent, or Firm* — Renner, Otto, Boisselle & Sklar, LLP.

(57) ABSTRACT

A rational construction technique of the lacrimal sac incision knife is disclosed. A Lacrimal sac incision knife is insertable into a nasal cavity of a patient, the lacrimal sac incision knife incising the lacrimal sac located in the back of the nasal cavity. A stabbing blade defines a lacrimal sac stabbing portion. A first side blade defines a first lacrimal sac incision portion and a second side blade defines a second lacrimal sac incision portion. A blade portion has a length size of approximately from 4.0 mm to 7.0 mm in a longitudinal direction, and a maximum width size of approximately from 1.4 mm to 2.0 mm in a width direction. The stabbing blade has a blade length size of approximately 1.2 mm in the longitudinal direction, and a maximum width size of approximately from 1.2 mm to 1.5 mm in the width direction. The first side blade and the second side blade respectively have a blade length size of approximately 3.0 mm to 5.0 mm in the longitudinal direction.

4 Claims, 12 Drawing Sheets

(56) References Cited

U.S. PATENT DOCUMENTS

| | | | | |
|---|---|---|---|---|
| 5,713,915 | A | 2/1998 | Van Heugten et al. | |
| 5,733,282 | A | 3/1998 | Ellman et al. | |
| 6,139,559 | A * | 10/2000 | Nordan | A61F 9/0133 606/166 |
| 6,908,471 | B2 | 6/2005 | Matsutani et al. | |
| 2003/0004527 | A1 | 1/2003 | Matsutani et al. | |
| 2005/0188548 | A1 | 9/2005 | Daskal et al. | |
| 2006/0217750 | A1 | 9/2006 | Ghannoum | |
| 2006/0281888 | A1 * | 12/2006 | Schlueter | C08F 257/02 526/318.44 |
| 2013/0053875 | A1 | 2/2013 | Scheller et al. | |
| 2014/0031847 | A1 * | 1/2014 | Mori | A61B 17/3211 606/167 |
| 2019/0262017 | A1 | 8/2019 | Haruna et al. | |

FOREIGN PATENT DOCUMENTS

| | | | |
|---|---|---|---|
| EP | 1262157 | A1 | 12/2002 |
| JP | 2002-345834 | A | 12/2002 |
| JP | 2013-150675 | A | 8/2013 |
| WO | 2005011744 | A2 | 2/2005 |
| WO | 2005011744 | A3 | 10/2005 |
| WO | 2018/070409 | A1 | 4/2018 |
| WO | 2019146632 | A1 | 8/2019 |

OTHER PUBLICATIONS

Written Opinion corresponding to International Application No. PCT/JP2021/014807 mailed Jun. 22, 2021, Japanese only.

International Preliminary Report on Patentability dated Apr. 7, 2021 in corresponding International Application No. PCT/JP2021/014807, with English Translation.

* cited by examiner

LACRIMAL SAC INCISION KNIFE

This application is a national phase of International Application No. PCT/JP2021/014807 filed Apr. 7, 2021, which claims the priority of Japanese Patent Application 2020-172726 filed Oct. 13, 2020, all of which are hereby incorporated herein by reference in their entireties.

TECHNICAL FIELD

The invention relates to a rational arrangement technique of a lacrimal sac incision knife.

BACKGROUND ART

As an example of a surgery instrument for head and neck region, a nose knife which is used by inserting into nasal cavity of the patient is known (for example, patent reference 1; WO2018/070409).

According to this known knife, as a structure effective for improving the operability during the nasal cavity surgery and for preventing interference with other combined surgery instrument such like an endoscope, a construction is known to have a shank portion with a straight part and a curved part. In this art, the shank portion is connected with the grip portion and the curved part is provided with a blade portion at the front end of the curve part.

By the way, as to the surgery by inserting knife into the nasal cavity of the patient, a surgical procedure to treat nasolacrimal duct obstruction is known. According to this surgical procedure, the knife (and the endoscope) approaches to the lacrimal sac via the bone window from the nasal cavity and thus, incision is made to the lacrimal sac. Namely, this surgical procedure is positioned at a border area between the ophthalmology and the otorhinolaryngology (Dacryocystorhinostomy: hereinafter referred to as "DCR method", especially "DCR intranasal method").

In such a case, according to the known nasal knife, while it can be preferably used to a surgery for the general nasal cavity as a relatively large surgery area, satisfactory usability is not guaranteed to an ophthalmology as a relatively small surgery area.

Namely, in the DCR method, when surgery approach is made to the ophthalmologic disease via the nasal cavity, further modification for improving the operability by the operator is desired over the known nasal knife.

PATENT REFERENCE

WO 2018/070409

DISCLOSURE OF THE INVENTION

Object to be Achieved by the Invention

This invention is made having regard to these aspects and the object of the invention is to provide with a construction technique of the lacrimal sac incision knife which can further improve the operability of the operator.

Embodiment to Achieve the Object

Above explained object can be achieved by the invention.

According to the invention, a lacrimal sac incision knife is provided. This lacrimal sac incision knife is insertable into nasal cavity of patient. The lacrimal sac incision knife incises the lacrimal sac located in the back of the nasal cavity. This lacrimal sac incision knife comprises a grip portion arranged to extend in a predetermined longitudinal direction to be held by user of the lacrimal sac incision knife, a shank portion connected to the grip portion, the shank portion entirely linearly extending in the longitudinal direction.

According to this inventio, the lacrimal sac incision knife entirely linearly extends in the longitudinal direction and as a result, approaching capability from the nasal cavity to the lacrimal sac as an ophthalmology region can securely be provided.

Especially, the shank portion entirely linearly extends in the longitudinal direction, any unintended injury risk can effectively be decreased when the lacrimal sac incision knife approaches in the nasal cavity.

Note that the feature "extending in the longitudinal direction" may preferably comprise aspects such like: extending in a direction slightly intersecting with the longitudinal direction, or extending substantially in the longitudinal direction including a slight curve or a slight step. As well, the feature "linearly" may preferably comprise aspects such like: extending in a direction slightly intersecting with the longitudinal direction, or extending substantially in the longitudinal direction including a slight curve or a slight step.

Further, the feature "entirely" may preferably comprise aspect substantially entirely extending but partly including intersecting region with the longitudinal direction or including non-linear region, The shank portion comprises a base portion extending in the longitudinal direction and a blade portion connected to the base portion at the front end region in the longitudinal direction. Same with the above aspect, by arranging both the base portion and the blade portion respectively to extend in the longitudinal direction, operability of the user and any decrease of unintended injury risk of the patient can effectively be secured when the lacrimal sac incision knife approaches to the lacrimal sac via the nasal cavity.

The blade portion comprises a stabbing blade provided at the front end region in the longitudinal direction and a pair of a first side blade and a second side blade, both the first side blade and the second side blade respectively being formed at both sides in the width direction and being connected with the stabbing blade.

The terminology "pair" is typically defined by a structure such that the first side bade and the second side blade are in symmetrical.

On the other hand, the stabbing blade defines a lacrimal sac stabbing portion which can be stabbed to the lacrimal sac in a state that the holding portion is held by the user.

Typically, the stabbing is conducted by having the lacrimal sac incision knife move in the longitudinal direction. The terminology of "move in the longitudinal direction" may broadly comprise aspects to have the lacrimal sac incision knife move substantially in the longitudinal direction. For example, it may preferably comprise movement in the slightly obliqued direction including the longitudinal direction component. Especially in the surgery of approaching to the lacrimal sac via the nasal cavity, operation in which the lacrimal sac incision knife does not perpendicularly approach to the lacrimal sac may possibly often take place. Having regard to these aspects, the stabbing blade according to this invention is preferably suitable to various operations, such like the operation perpendicularly or obliquely stabbing the lacrimal sac and then, incise the lacrimal sac in the face direction of the lacrimal sac, or the multiple operation perpendicularly or obliquely stabbing the lacrimal sac and at the same time incising the lacrimal sac.

Further, it does not exclude the operation of only incising the lacrimal sac without stabbing operation.

Further, the stabbing blade may typically preferably be arranged to be symmetrical pair structure such that the stabbing blade is connected with each of the first side blade and the second side blade, respectively. Moreover, by appropriately setting the opening angle of stabbing blades and setting the connecting angle of the stabbing blade to the first side blade and the second side blade, blade group can be provided such that the pair of the stabbing blades and the pair of the first side blades (namely, the first side blade and the second side blade) respectively extends to different directions. By such construction, when incising the lacrimal sac, appropriate blade can be selected in accordance with the complicated shape of the lacrimal sac and as a result, usability of the lacrimal sac incision knife can be improved.

One of the first side blade and the second side blade defines a first lacrimal sac incision portion which incises the lacrimal sac in any one side of the longitudinal direction of the lacrimal sac as the lacrimal sac knife is operated to move in any one side of the width direction, In this case, following aspects may preferably be comprised such that the lacrimal sac is incised by using any one of the first side blade and the second side blade without using the stabbing blade, and such that the lacrimal sac is incised by using any one of the first side blade and the second side blade after slightly stabbing the lacrimal sac by the stabbing blade (or by the connecting region with the stabbing blade).

The other of the first side blade and the second side blade defines a second lacrimal sac incision portion which incises the lacrimal sac in the other side of the longitudinal direction of the lacrimal sac, as the state is kept such that the hold portion is held by the user and as the lacrimal sac knife is operated to move in the other side of the width direction. In this case, both the aspect also to use the stabbing blade and the aspect not to use the stabbing blade can preferably be comprised.

The "one" and the "other" of longitudinal extending direction of the lacrimal sac are typically be defined by an aspect of opposing to each other by 180 degrees. However, the aspect of intersecting to each other by any angle other than 180 degrees may be comprised. Further, for example, an aspect may be comprised such that the lacrimal sac is multiply incised in the direction intersecting the longitudinal extending direction to open the incised region (such type of the surgery is called as "petal type" or "flower petal type").

Moreover, as to the direction, various types may be comprised for example to incise the lacrimal sac step by step or in a curved manner or in a zigzag manner. Further, the direction is required only to comprise at least a component of the longitudinal extending direction of the lacrimal sac and aspect to incise the lacrimal sac in the other direction may also be comprised.

The terminology of "the state is kept such that the hold portion is held by the user" is defined such that the gripping state is kept without changing the gripping hand of the grip portion when incising the lacrimal sac in any one of the direction or in the other direction. By this, it is not necessary to change the gripping hand when changing the incising direction after the stabbing as is the case of the single edged knife (for example changing by 180 degrees). Thus, necessity of changing the gripping hand can be abbreviated and as a result, usability in the ophthalmologic field via the nasal cavity as relatively narrow operation area can be improved.

Further, in a case that the lacrimal sac is incised by the above explained petal type or the flower petal type, the user is not required to change the gripping hand of the grip portion and can conduct multiple incise operations to multiple directions in a precise and quick manner. As a result, the usability of the lacrimal sac incision knife can further be improved.

Further, as to the lacrimal sac incision knife according to the invention, the specific size of the component parts is optimized in accordance with the size of the lacrimal sac as the surgery object. While the size of the lacrimal sac deviates in general based on individual difference, the invention optimizes the size so as to correspond to such difference specifically as follows:

The blade portion has a length size of approximately from 3.0 mm to 10.0 mm in the longitudinal direction, a maximum width size of approximately from 1.0 mm to 2.0 mm in the width direction.

The stabbing blade has a blade length size of approximately 1.0 mm to 4.0 mm in the longitudinal direction, a maximum width size of approximately from 1.0 mm to 2.0 mm in the width direction.

The first side blade and the second side blade respectively have a blade length size of approximately 2.0 mm to 6.0 mm in the longitudinal direction.

As a further preferable aspect of the invention, with respect to the lacrimal sac incision knife as explained above, the base portion may be arranged to have a length in the longitudinal direction approximately twice as long as the length of the blade portion.

By such construction, the rigidity of the base portion can be improved maintaining the operability of the lacrimal sac incision knife.

As a further preferable aspect of the invention, with respect to the lacrimal sac incision knife as explained above, the shank portion may be arranged to have a length in the longitudinal direction as from approximately 15.0 mm (millimeter) to approximately 50.0 mm, and the base portion is arranged to have a length in the longitudinal direction as from approximately 5.0 mm to approximately 47.0 mm, As a further preferable aspect of the invention, with respect to the lacrimal sac incision knife as explained above, each of the first side blade and the second side blade may be arranged such that the closer to the stabbing blade, the gradually narrower the width becomes in the width direction.

By such construction, stabbing capability and incision capability can further be improved.

As a further preferable aspect of the invention, with respect to the lacrimal sac incision knife as explained above, the base portion may be arranged to comprise a taper portion such that the closer to the blade portion, the gradually thinner the thickness of the taper portion becomes in the longitudinal direction. And the region where the first side blade and the second side blade are formed may be arranged such that the thickness of this region is constant.

The terminology of "gradually" is substantially defined as "sequentially", "one by one" or "one after another". The invention may preferably comprise not only the aspect of entirely and constantly gradually becoming thinner, but also the aspect that the decreasing ratio changes or the aspect of partly gradually becoming thinner.

By such construction, with respect to the base portion, a high rigidity provided region for the lacrimal sac incision knife can be provided. On the other hand, with respect to the blade region where the first side plate and the second side plate are formed, lacrimal sac incision operability improved region with thin thickness can be provided. Further, the taper portion the thickness of which gradually decreases connects the high rigidity provided region with the lacrimal sac incision operability improved region. As a result, smooth operability of the lacrimal sac incision knife moving in the nasal cavity can be secured.

As a further preferable aspect of the invention, with respect to the lacrimal sac incision knife as explained above, the taper portion is arranged to have a length in the longitudinal direction as from approximately 3.0 mm (millimeter) to approximately 7.0 mm, the taper portion is connected with the blade portion such that the thickness of the taper portion is gradually decreased from approximately 0.3 mm to approximately 0.15 mm as get closer to the blade portion, and the region of the blade portion where the first side blade and the second side blade are formed is arranged to have a thickness of approximately 0.15 mm in the longitudinal direction.

By such construction, the above-explained high rigidity provided region and the lacrimal sac incision operability improved region can rationally be provided.

Note that, as to the size of each component part of the lacrimal sac incision knife as explained above, for example, following typical value may preferably be adopted in order to effectively provide the invention in the actual product design. Namely:

The blade portion may have a length size of approximately 5.7 mm in the longitudinal direction, a maximum width size of approximately 1.7 mm in the width direction.

The stabbing blade may have a blade length size of approximately 1.2 mm in the longitudinal direction, a maximum width size of approximately 1.4 mm in the width direction.

The first side blade and the second side blade may respectively have a blade length size of approximately 4.5 mm in the longitudinal direction.

The shank portion may have a length in the longitudinal direction as approximately 17.3 mm.

The base portion may have a length in the longitudinal direction as approximately 11.6 mm.

The taper portion may have a length in the longitudinal direction as approximately 5 mm.

The taper portion may be connected with the blade portion such that the thickness of the taper portion is gradually decreased from approximately 0.3 mm to approximately 0.15 mm as get closer to the blade portion and the region of the blade portion where the first side blade and the second side blade are formed may have a thickness of approximately 0.15 mm in the longitudinal direction.

According to the invention, a rational construction technique of the lacrimal sac incision knife is provided.

Representative Embodiment to Exploit the Invention

Representative Embodiment of the Invention

A representative embodiment of the invention is explained according to FIG. 1 to FIG. 12.

In figures, the structure of the lacrimal sac incision knife 1 according to the embodiment is respectively shown in FIG. 1 to FIG. 8 and schematic aspect of the surgery operation by using the lacrimal sac incision knife 1 is shown in FIG. 9 to FIG. 12.

With respect to the structure of the lacrimal sac incision knife 1; FIG. 1 and FIG. 2 are a plan view and a front view respectively showing the entire structure, FIG. 3 and FIG. 4 are schematic plan views respectively showing the structure of the front end region of the lacrimal sac incision knife 1, FIG. 5 and FIG. 6 are a schematic front view and a schematic cross sectional view respectively showing the structure of the front end region, FIG. 7 is a schematic plan view showing the structure of a blade portion and FIG. 8 is a schematic cross sectional view showing the structure of the front end region.

(Definition of Directions)

With respect to FIGS. 1 to 8, as a sake of convenience for the explanation, the longitudinal direction of the lacrimal sac incision knife 1 is defined as "L", longitudinal front side is defined as "LF", longitudinal rear side is defined as "LR", width direction is defined as "W", upper side on the paper in FIG. 1 and FIG. 3 is defined as "width right side direction WR", lower side on the paper is defined as "width left side direction WL", upper-lower direction on paper in FIG. 2, FIG. 5 and FIG. 6 is defined as "vertical direction V".

(Entire Structure of the Lacrimal Sac Incision Knife)

The lacrimal sac incision knife 1 according to the embodiment is arranged mainly to comprise a grip portion 2 and a shank portion 3. Each of the grip portion 2 and the shank portion 3 is provided with elongated body to extend in the longitudinal direction L. Further, the lacrimal sac incision knife 1 as itself is also provided with elongated body and also extends in the longitudinal direction L.

In this embodiment, the grip portion 2 is made of resin, while the shank portion 3 is made of metal.

(Structure of the Shank Portion 3)

As shown in FIG. 3, the shank portion 3 is mainly provided with a base portion 4 and a blade portion 6. The base portion 4 is connected with the grip portion 2 to be gripped by the operator (the operator is not shown in drawings for the sake of convenience) in the front side direction LF of the longitudinal direction L. The blade portion 6 is connected with the base portion 4 in the front side direction LF as a cutting means.

(Structure of the Base Portion 4)

The base portion 4 is arranged to have substantially a constant width in the width direction as shown in FIG. 3 (see reference W3 in FIG. 7 as will be explained later). The base portion 4 is provided with a step 5 at the intermediate region. Further, as shown in FIG. 6, with respect to the upper lower direction V from the step 5 to the blade portion 6, a taper portion 41 is provided.

The taper portion 41 according to this embodiment is arranged to have a relatively large decrease rate of the thickness in the vicinity of the step 5 and to have a relatively small and constant decrease rate of the thickness at a region apart from the step 5 and close to the blade portion 6.

(Structure of the Blade Portion 6)

The blade portion 6 comprises a stabbing blade 60, a first side blade 61 and a second side blade 62. The stabbing blade 60 is formed at the most front end region of the front side direction LF. The first side blade 61 is formed at the width right side direction WR of the blade portion 6, while the second side blade 62 is formed at the width left side direction WL of the blade portion 6. The first side blade 61 and the second side blade 62 are arranged to be a pair and continuously formed with the stabbing blade 60.

As shown in FIG. 7 in greater detail, with respect to the longitudinal direction L, the blade portion 6 has a length L1, the stabbing blade 60 has a length L2, each of the first side blade 61 and the second side blade 62 has a length L3, respectively. In other words, a relation is arranged such that "L1=L2+L3".

On the other hand, as shown in FIG. 7, the stabbing blade 60 has a width W1 in the width direction W. Further, each of the first side blade 61 and the second side blade 62 has a width W1 at the connecting region to the stabbing blade 60 and has a width W2 at the connecting region to the base portion 4, respectively.

In this embodiment, a relation is arranged such that W1 is smaller than W2 (W1<W2). As to the relation between two widths, for example relation such that W1 is equal to W2, or relation such that W1 is larger than W2 can be adopted.

Further, each of the first side blade 61 and the second side blade 62 is arranged to have a taper shape, the width of which gradually increases from the width W1 as a front side (namely narrow width region) to the width W2 as a rear side (namely broad width region).

By adopting such construction, when lacrimal sac incision surgery is conducted (which will be explained later), the stabbing blade 60 with narrow width improves the stabbing operability to the lacrimal sac, while each front regions of the first side blade 61 and the second side blade 62 with narrow width improves the incision operability to the lacrimal sac. Further, because each of the first side blade 61 and the second side blade 62 has a taper which gradually increases its width as close to the rear side direction LB, both the stabbing capability and the incision capability are further improved.

Moreover, the width W2 of each of the first side blade 61 and the second side blade 62 is respectively arranged to be larger than the width W3 of the base portion 4. Namely, with respect to the width direction W, each of the first side blade 61 and the second side blade 62 respectively projects from the base portion 4 by a small amount. By such construction, stabbing and incision capability can be further improved when the lacrimal sac incision surgery which will be explained later is conducted.

Note that, as to such width, an aspect such that W2=W3, or W2<W3 can appropriately be adopted.

(Dimension of Each Component)

With respect to the specific dimension of each component parts of the lacrimal sac incision knife 1, following spec is given as shown in FIG. 3, FIG. 7, FIG. 8 and so on (each unit of the dimension is "mm": millimeter). The blade portion 6 is arranged to have a length L1 of approximately 5.7 mm and a maximum width W2 of approximately 1.7 mm in the width direction W.

The stabbing blade 60 is arranged to have a length L2 of approximately 1.2 mm in the longitudinal direction L and a maximum width W1 of approximately 1.4 mm in the width direction W.

Each of the first side blade 61 and the second side blade 62 is arranged to have a length L3 of approximately 4.5 mm in the longitudinal direction L, a minimum width of approximately 1.4 mm in the width direction W (to be connected to the stabbing blade 60 at this minimum width), and a maximum width W2 of approximately 1.7 mm in the width direction W. In other words, the maximum width W2 of the first side blade 61 and the second side blade 62 defines the maximum dimension size of the blade portion 6 (approximately 1.7 mm according to this embodiment).

Further, as shown in FIG. 3, the base portion 4 has a length LB of approximately 11.6 mm in the longitudinal direction L which is approximately two times longer than the blade portion 6 and has a width W3 of approximately 1.4 mm to 2.0 mm.

Further, as shown in FIG. 3, the shank portion 3 has a length LS of approximately 17.3 mm in the longitudinal direction.

Further, as shown in FIG. 8, the taper portion 41 has a length LT of approximately 5 mm in the longitudinal direction L. And the taper portion 41 is connected with the blade portion 6 such that the thickness of the taper portion 41 gradually decreases from the maximum thickness TH2 of approximately 0.3 mm to the minimum thickness TH1 of approximately 0.15 mm. And as shown in FIG. 8, the forming region L1 of the first side blade 61 and the second side blade 62 is arranged to have a thickness TH1 of approximately 0.15 mm in the longitudinal direction L.

Next, specific example of lacrimal sac incision surgery by using the lacrimal sac incision knife 1 according to this embodiment is explained in reference of FIG. 9 to FIG. 12. In this embodiment, as an example, dacryocystorhinostomy (DCR method) surgery is explained in which lacrimal sac incision is made by using the lacrimal sac incision knife 1 via the nasal cavity and the bone window to cure the nasolacrimal duct obstruction.

(Structure of the Surgical Area)

FIG. 9 schematically shows an abstract of the eye and nose regions of the patient P as an object of this surgery. In the eye P1 and the nose P2 regions of the patient P, nasal cavity P4 as a space in the nose extends along the nasal cavity extending direction from the nostrils P3 which is defined as an opening hole to the outside. The lacrimal sac R4 is disposed in the vicinity of the nasal cavity P4 such that the bone window P5 intervenes at the back side of the nasal cavity P4 (upper side in FIG. 9). Note that, while the bone window P5 is formed by using drill before the surgery, such forming method pertains to a known art and therefore, detailed explanation is abbreviated.

(Structure of the Eye Region)

On the other hand, with respect to the eye P1 of the patient P, lacrimal grand R1 is connected and the eye P1 is connected with the lacrimal sac R4 via the puncta R2 and the canaliculus R3 and also connected with the nasal cavity P4 via the nasolacrimal duct R6. By such structure, tears are transferred to the nasal cavity P4 via the lacrimal gland R1, the eye P1, the puncta R2, the canaliculus R3, the lacrimal sac R4 and the nasolacrimal duct.

(Abstract of the DCR Method)

Above mentioned DCR method typically provides with an incision surgery to the lacrimal sac R4 as an example of the nasolacrimal duct obstruction. The lacrimal sac incision knife 1 according to this embodiment is inserted to the nasal cavity P4 with the endoscope from the nostrils P3 in FIG. 9 and then, moves to the back side substantially along with the nasal cavity extending direction P4L and finally, reaches the lacrimal sac R4 via the bone window P5. Note that the endoscope is not shown in drawings for the sake of convenience.

The lacrimal sac R4 has an elongated shape with a long axis and a short axis. While individual difference does exist, the length in the longitudinal extending direction (longitudinal direction of the lacrimal sac R4) is arranged to be approximately from 6.0 mm to 15.5 mm.

(Approach to the Lacrimal Sac R4)

As shown in FIG. 10, the stabbing blade 60 of the lacrimal sac incision knife approaches to the incision area R5S defined as the central part of the surgical area R5 (namely, the lacrimal sac R4) by operating the lacrimal sac incision knife 1 to move in the longitudinal direction. Note that, in the actual surgery, while the lacrimal sac incision knife 1 sometimes does not approaches to the lacrimal sac R4 in a perpendicular manner, this embodiment shows the perpendicular approach for the sake of convenience.

(Incision of the Lacrimal Sac R4 in One of the Longitudinal Directions)

Then, as shown in FIG. 11, the lacrimal sac incision knife 1 is moved in the direction R5L 1 as one side of the longitudinal direction of the lacrimal sac R4 and incises the lacrimal sac R4 by using the first side blade 61. Namely, the first side blade 61 defines a first lacrimal sac incising part. At this stage, the user can conduct the incision operation by the first side blade 61 keeping the grip as the lacrimal sac incision knife 1 is approached to the lacrimal sac (without changing the grip).

(Incision of the Lacrimal Sac R4 in Other of the Longitudinal Directions)

Then, as shown in FIG. 12, the lacrimal sac incision knife 1 is moved in the other direction R5L2 (left side in FIG. 12) as the other side of the longitudinal direction of the lacrimal sac R4 and further incises the lacrimal sac R4 by using the second side blade 62. Namely, the second side blade 62 defines a second lacrimal sac incising part. At this stage, the user can conduct the incision operation by the second side blade 62 keeping the grip as the lacrimal sac incision knife 1 incised in the direction R5L1 by using the first side blade 61 (without changing the grip).

Namely, the lacrimal sac incision knife 1 according to this embodiment, the first side blade 61 and the second side blade 62 are provided as a double edged structure and are arranged to be connected continuously to the stabbing blade 60, respectively. Thus, the user can conduct the incision operation to the lacrimal sac R4 both in the right and left side (namely both longitudinal directions R5L1 and R5L2 of the lacrimal sac R4) without inverting the lacrimal sac incision knife 1 by changing the grip of the grip portion 2 in each occasion of switching the operation.

Further, as shown in FIG. 6, the lacrimal sac knife 1 according to this embodiment is provided with the taper portion 41, the thickness of which gradually decreases as being close to the longitudinal front side direction LF with respect to the vertical direction V from the step portion 5 to the blade portion 6.

And as shown in FIG. 8, the base portion 4 is provided with a rigidity securing region A (thickness TH2). On the other hand, the blade portion 6 is provided with a lacrimal sac incision operability improved region B. Further, the taper portion 41 the thickness of which gradually decreases connects the rigidity securing region A with the lacrimal sac incision operability improved region B. As a result, the lacrimal sac incision knife 1 can be provided to have smoothness in moving in the nasal cavity P4 (see FIG. 9).

Further, each of the first side blade 61 and the second side blade 62 is arranged to have multiple blades structure with contiguous and multiple directions (see FIG. 7 and so on).

Therefore, the surgery operation can be conducted from the approach to the above-explained lacrimal sac R4 to the completion of the incision by appropriately selecting the blade from the multiple blades structure with different directions. As a result, the lacrimal sac incision knife 1 can be applied to the complicated shape of the lacrimal sac and thus, operability can further be improved.

Note that, according to this embodiment, the lacrimal sac incision knife 1 approaches to the lacrimal sac R4 and then, the incision is made by the first side blade 61 and then, by the second side blade 62. However, the operation aspect of the lacrimal sac incision knife 1 is not limited to such process.

For example, the user may incise the lacrimal sac R4 by using the first side blade 61 to multiple directions including the longitudinal direction R5L1 and then, may open the lacrimal sac R4 being incised. And then, the user may incise the lacrimal sac R4 by using the second side blade 62 to multiple directions including the longitudinal direction R5L2 and then, may open the lacrimal sac R4. By these steps, the lacrimal sac R4 can be incised like opening flower ("petal type" or "flower petal type").

Otherwise, incision aspect such that stabbing the lacrimal sac R4 by the stabbing blade 60 and then, incising the lacrimal sac R4 in the face direction can preferably be adopted.

According to the above explained embodiment, a construction technique of the lacrimal sac incision knife 1 which can further improve the operability of the operator is provided.

BRIEF EXPLANATION OF DRAWINGS

Same with the FIG. 3.

Same with FIG. 11.

EXPLANATION OF REFERENCES

Figure 1:
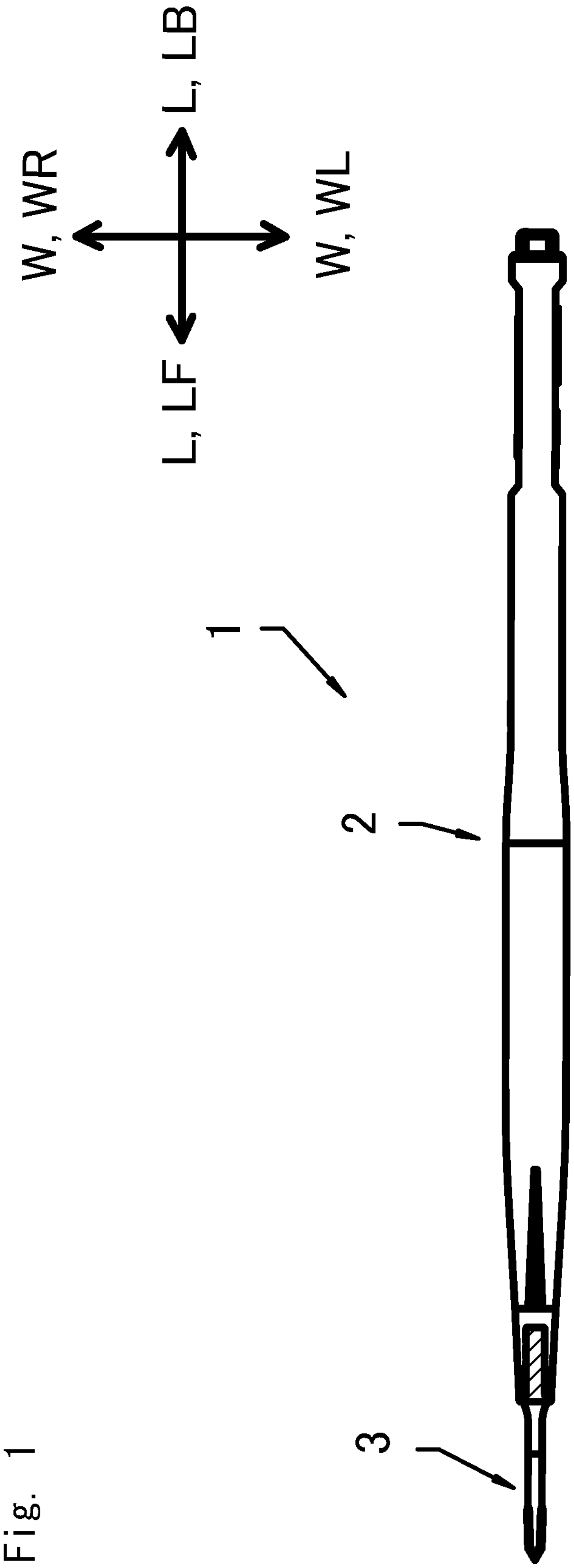
FIG. 1 is a plan view of the entire structure of the lacrimal sac incision knife 1 according to the embodiment of the invention.
Figure 2:
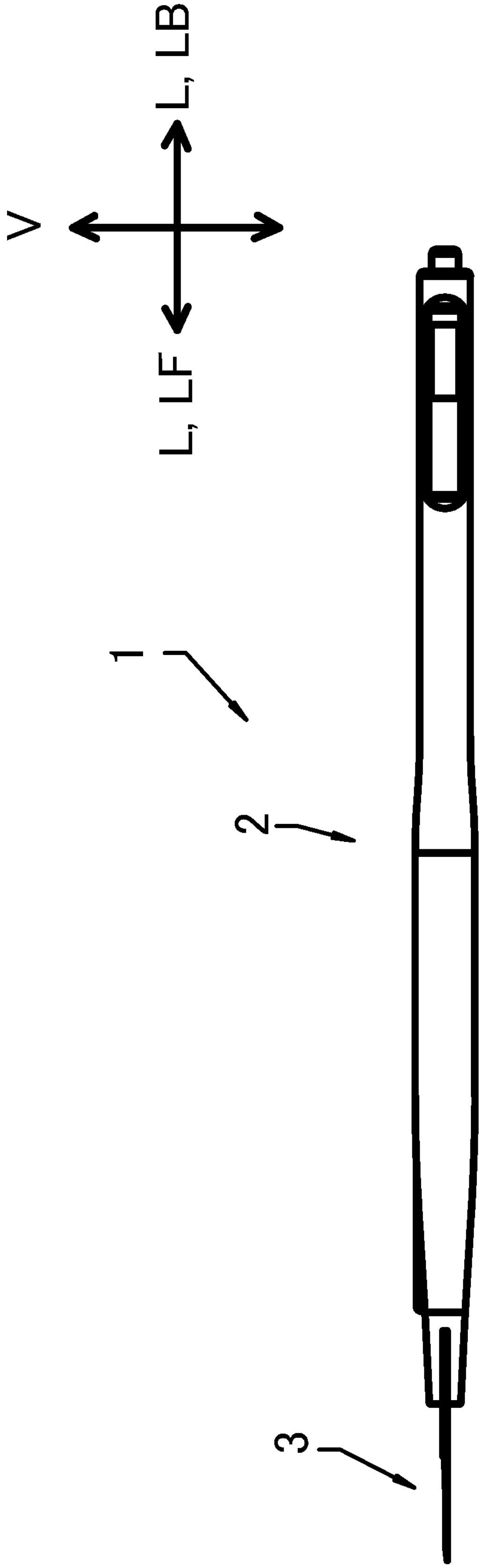
FIG. 2 is a front view which shows the entire structure of the lacrimal sac incision knife 1 according to the embodiment of the invention.
Figure 3:
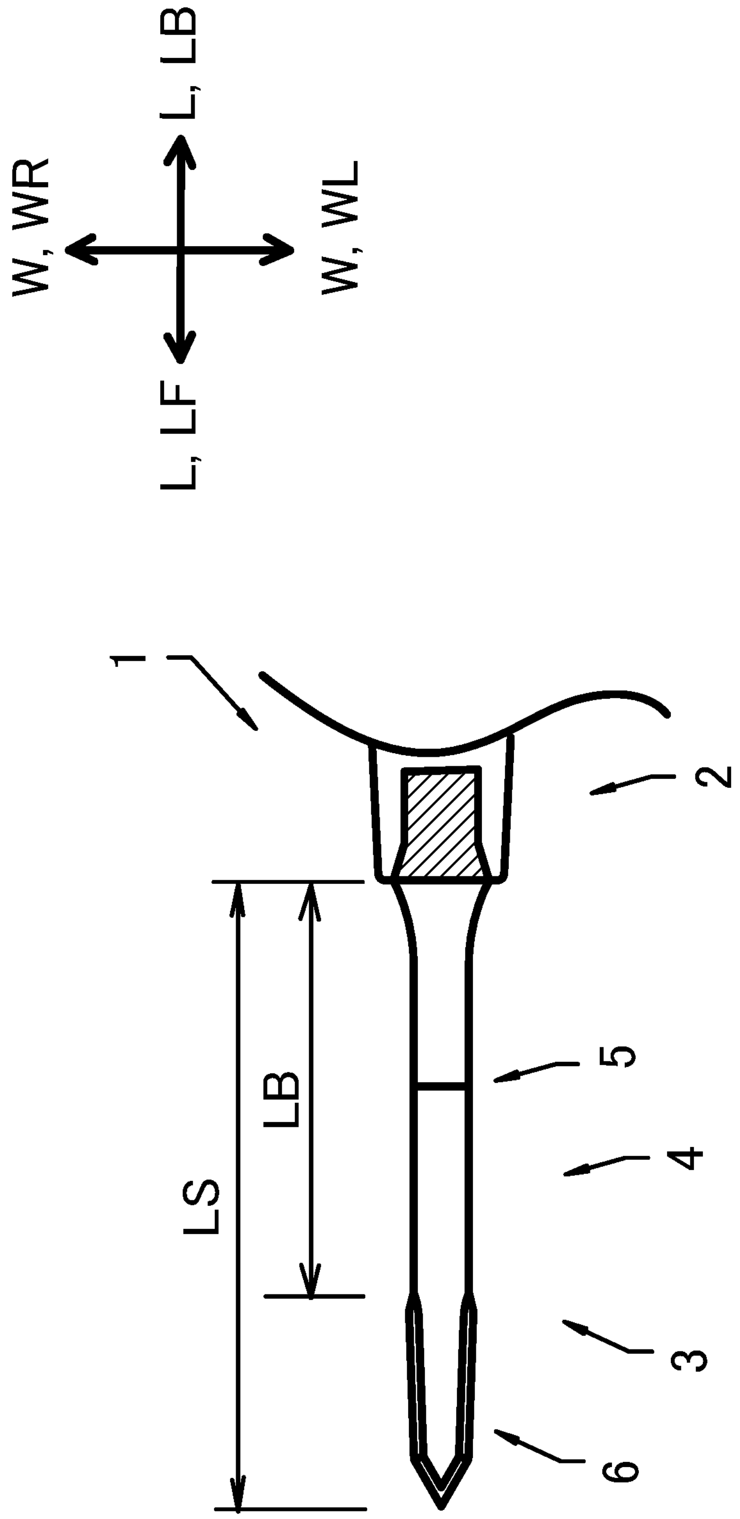
FIG. 3 is a schematic plan view which shows the structure of the front end region of the lacrimal sac incision knife 1.
Figure 4:
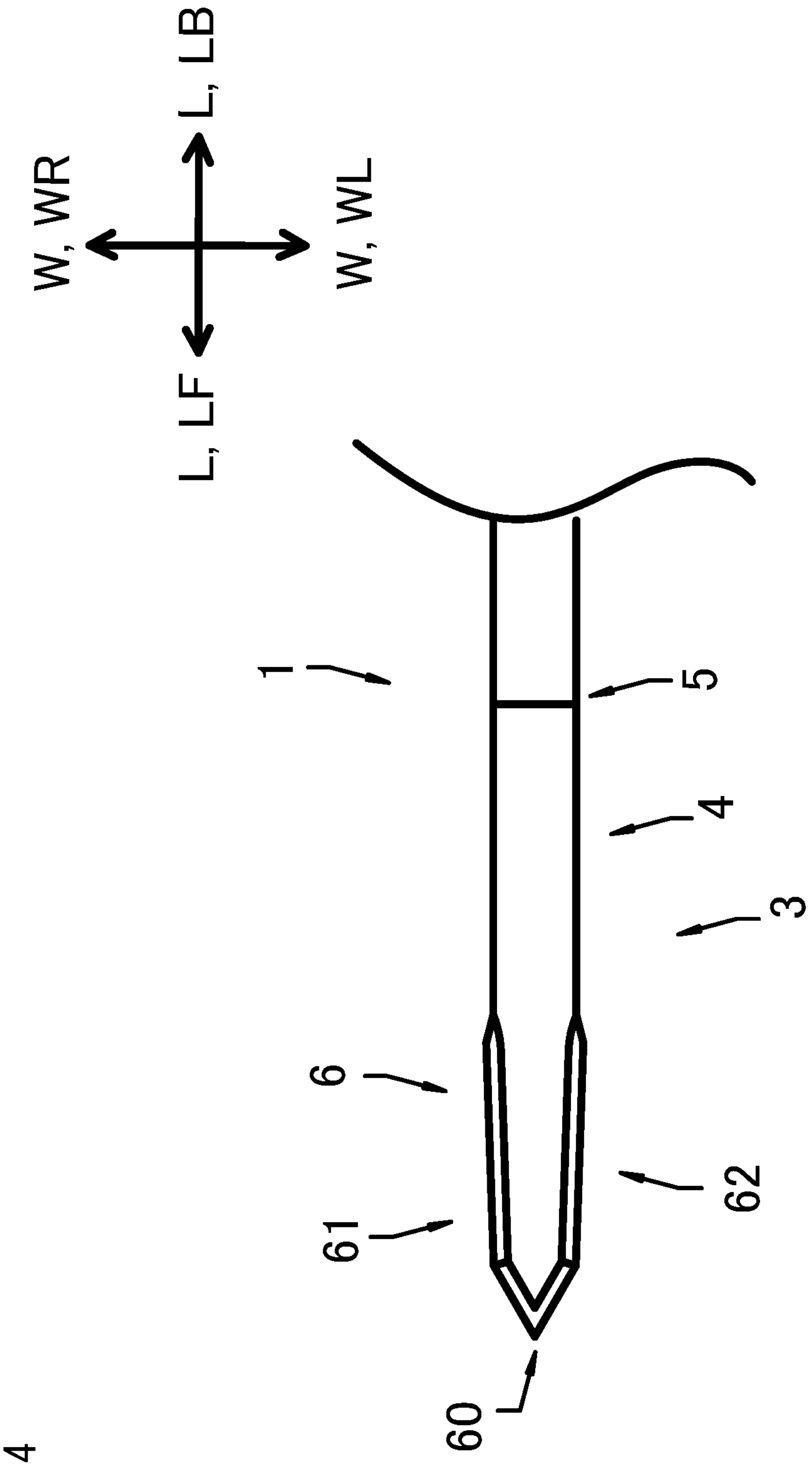
FIG. 4 is a schematic plan view which shows the structure of the front end region of the lacrimal sac incision knife 1.
Figure 5:
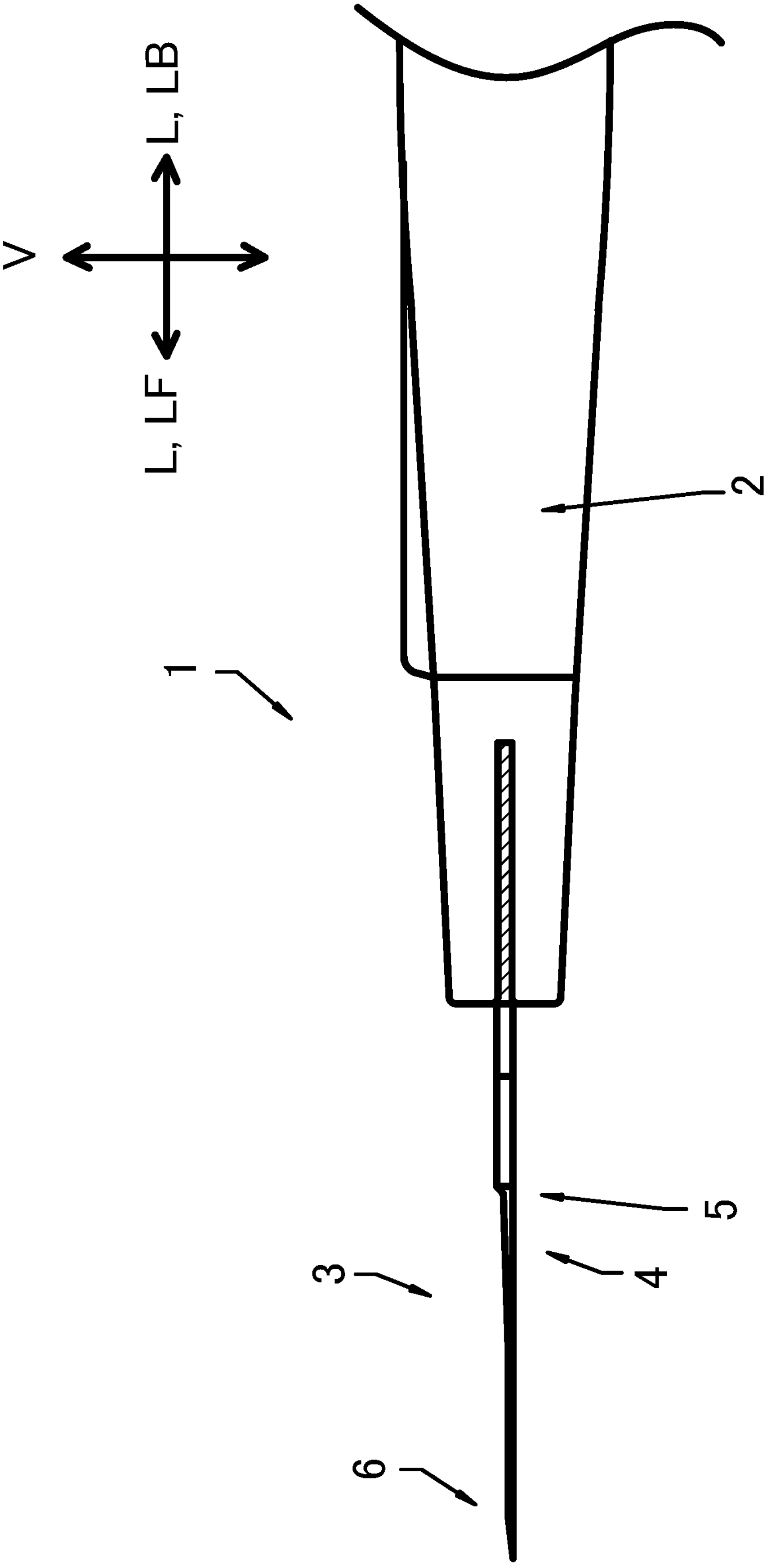
FIG. 5 is a schematic front view which shows the structure of the front end region of the lacrimal sac incision knife 1.
Figure 6:
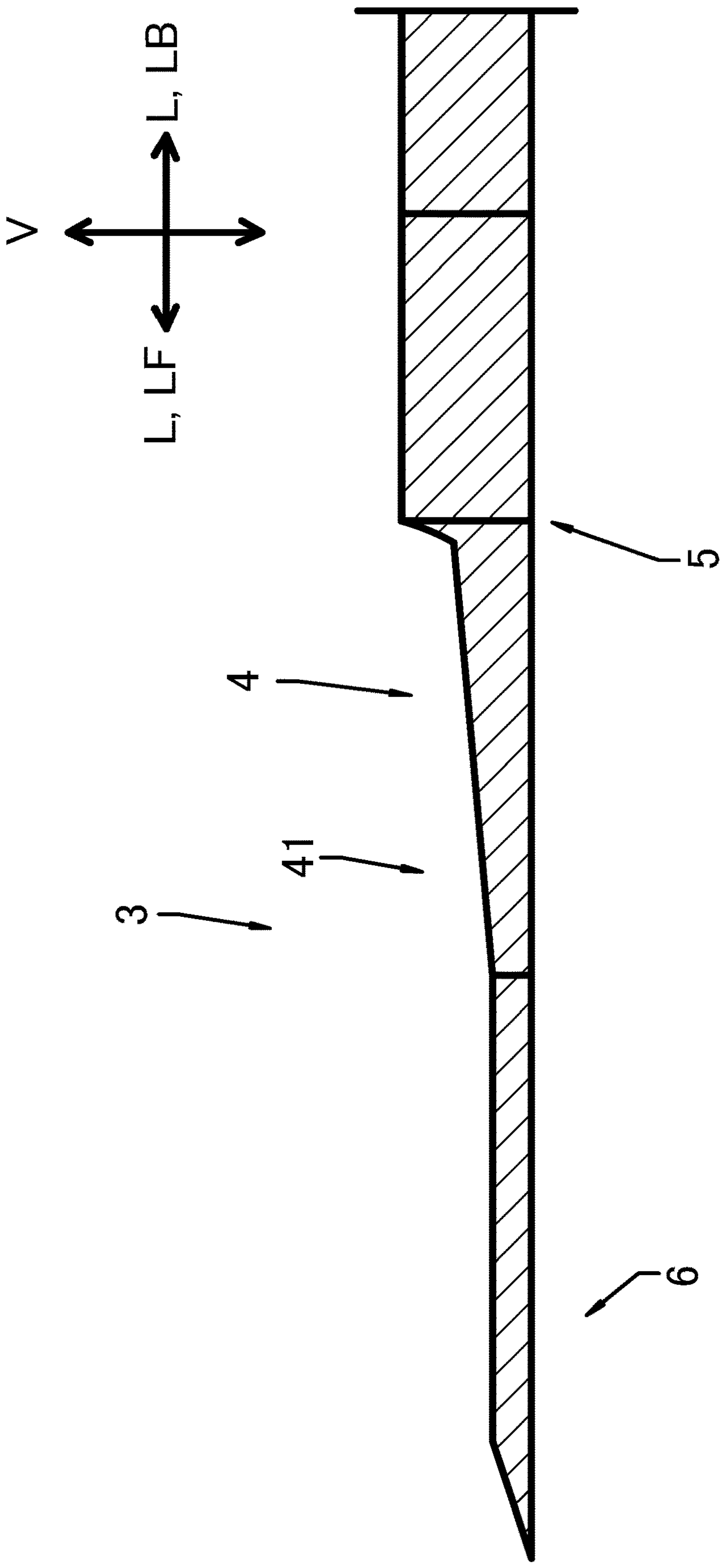
FIG. 6 is a schematic cross sectional view which shows the structure of the front end region of the lacrimal sac incision knife 1.
Figure 7:
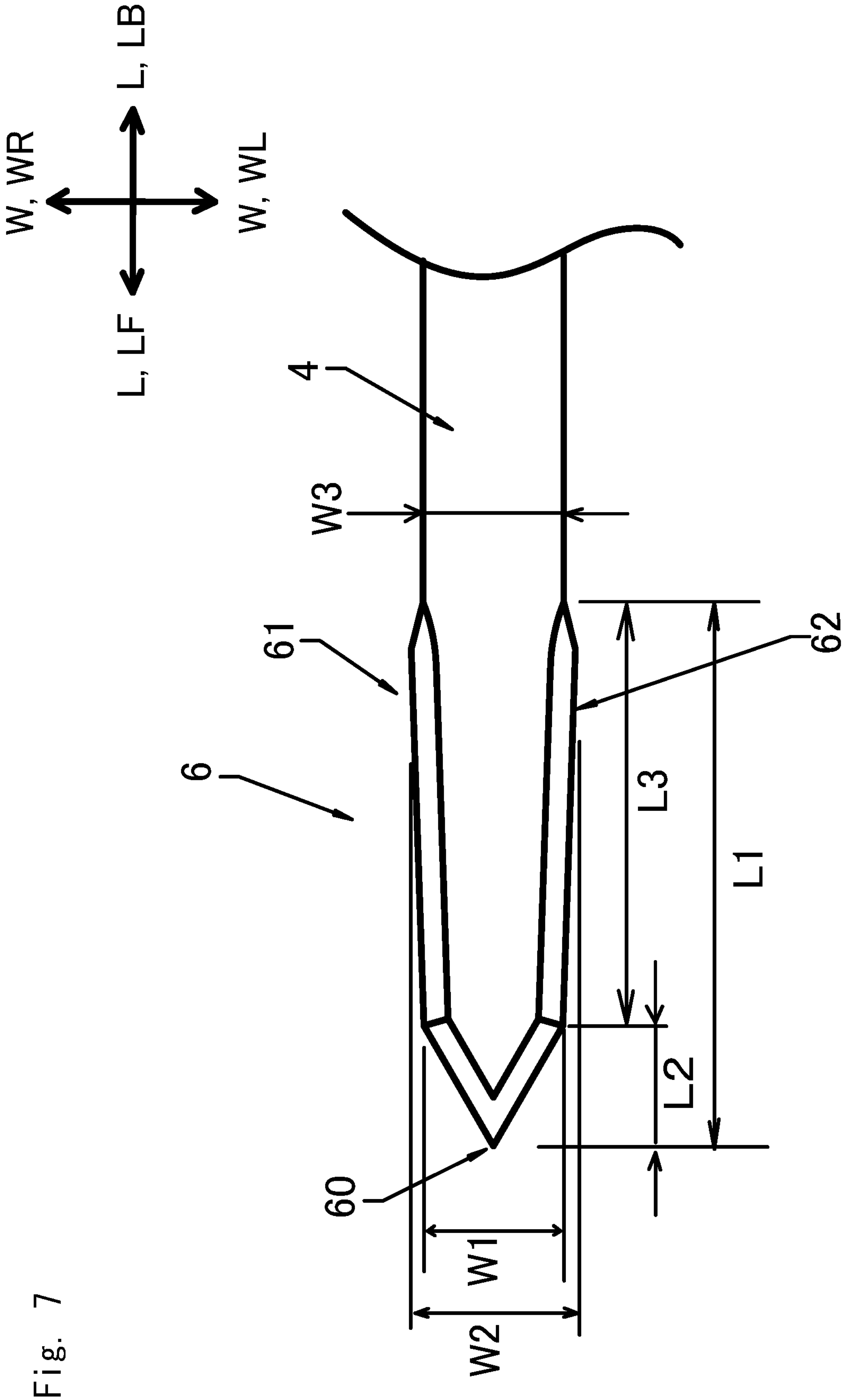
FIG. 7 is a schematic plan view which shows the structure of the blade portion 6 of the lacrimal sac incision knife 1.
Figure 8:
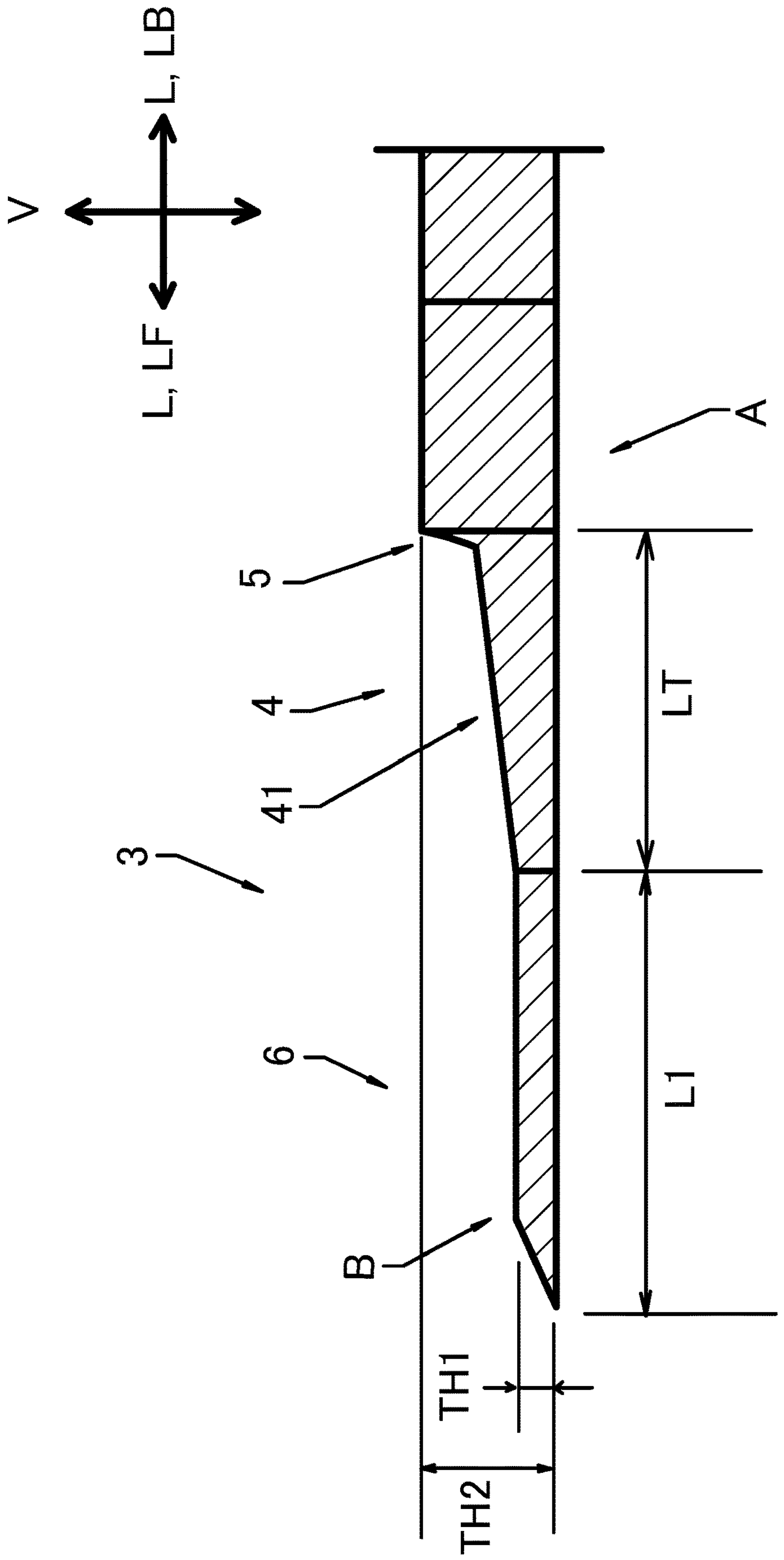
FIG. 8 is a schematic cross sectional view which shows the structure of the front end region of the lacrimal sac incision knife 1.
Figure 9:
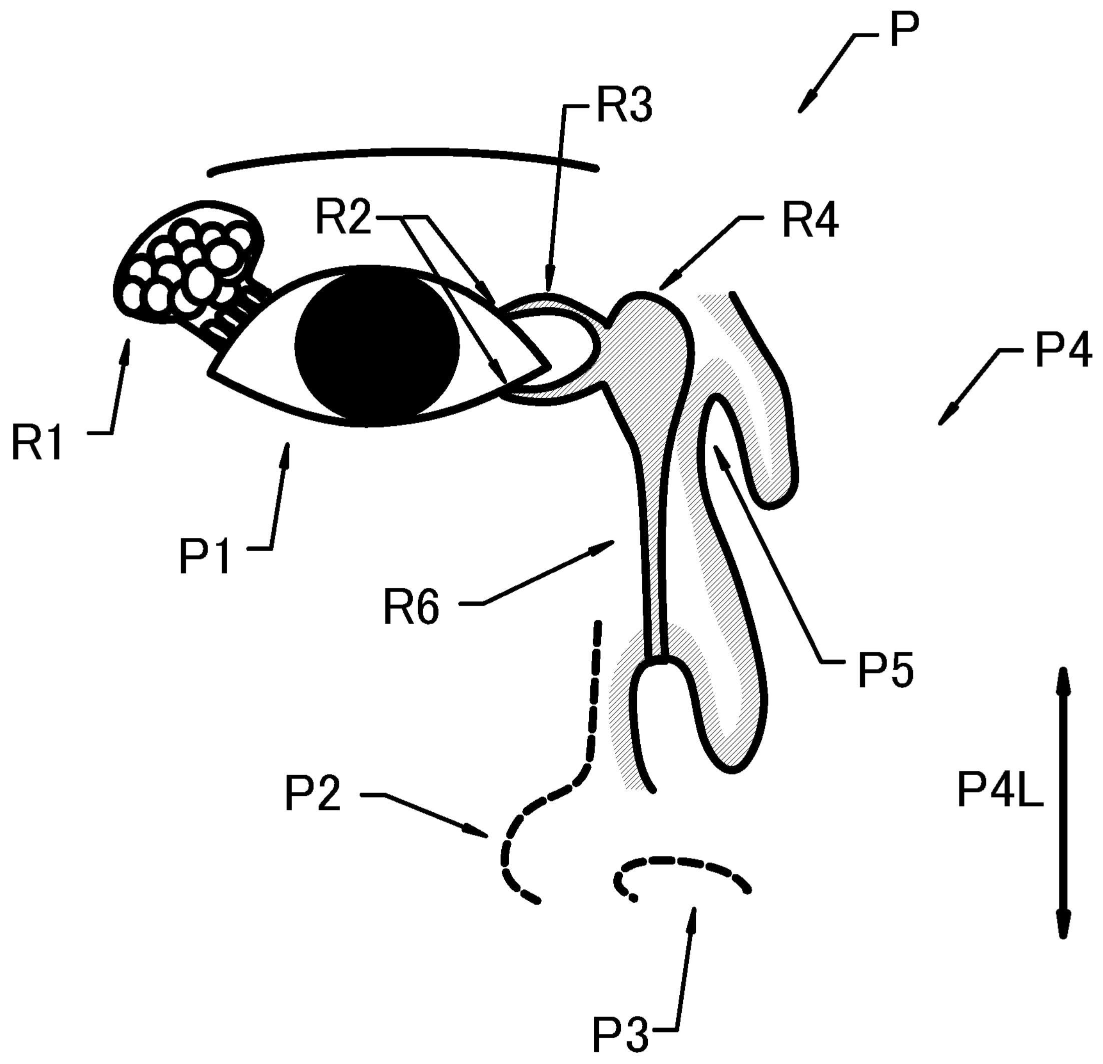
FIG. 9 is a schematic view which shows eye and nose regions of the patient P as an object of the surgical operation by using the lacrimal sac incision knife 1 according to the embodiment of the invention.
Figure 10:
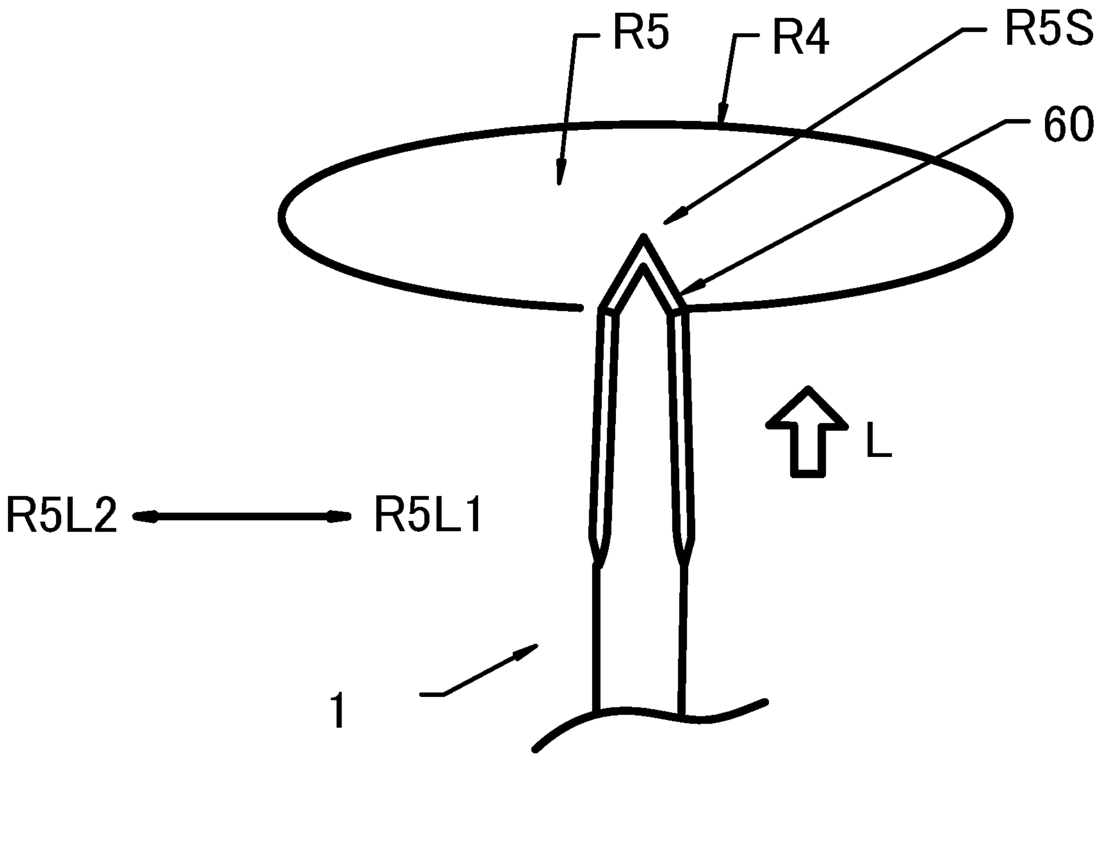
FIG. 10 is a schematic view which shows operational state (approaching state) of the lacrimal sac incision knife 1 to the lacrimal sac R4 as the surgical area R5.
Figure 11:
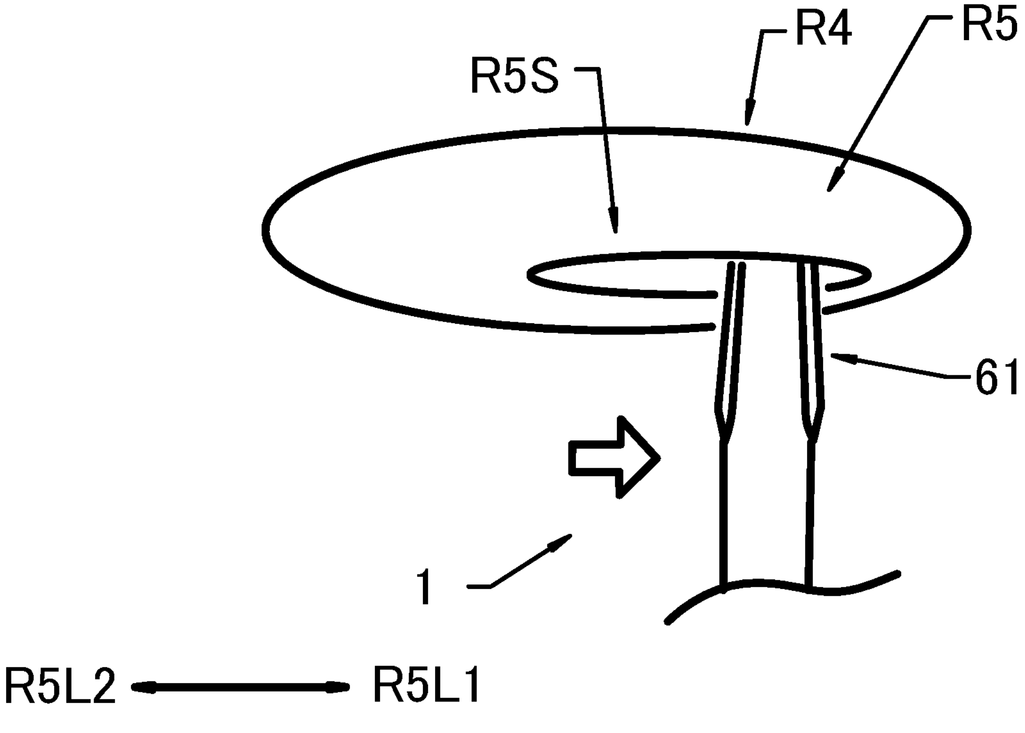
FIG. 11 is a schematic view which shows incisional state of the lacrimal sac R4.
Figure 12:
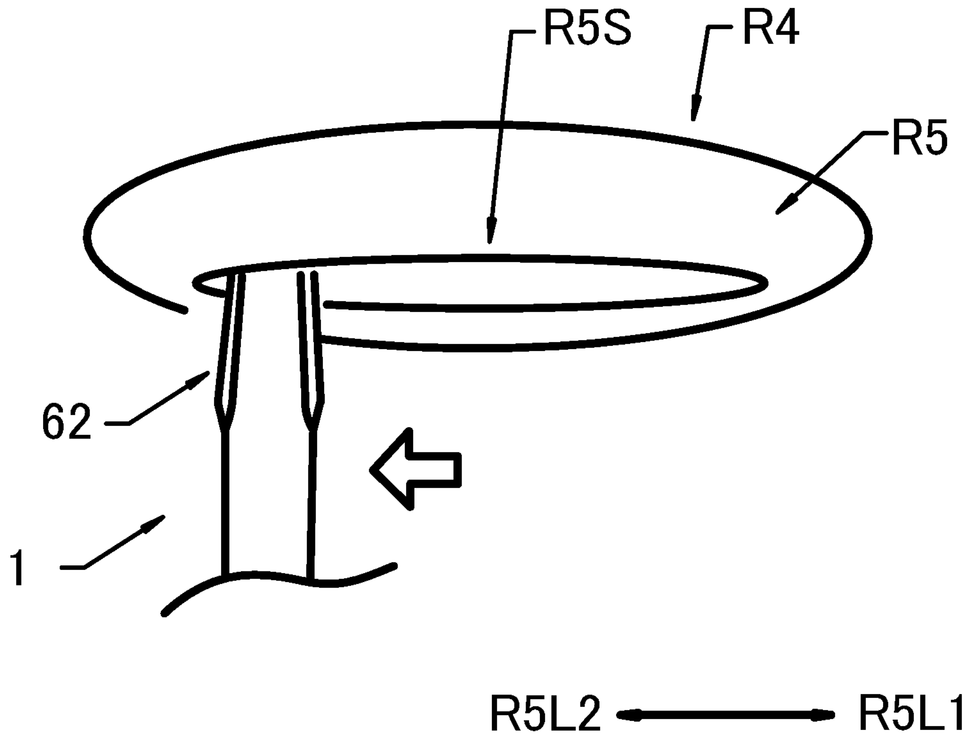
FIG. 12 is a schematic view which shows incisional state of the lacrimal sac R4

1 Lacrimal sac incision knife
2 Grip portion
3 Shank portion
4 Base portion
41 Taper portion
5 Step portion
6 Blade portion
60 Stabbing blade
61 First side blade
62 Second side blade
L Longitudinal direction
LF Front side direction of the longitudinal direction
LB Rear side direction of the longitudinal direction
W Width direction WR Width right side direction
WL Width left side direction
V Vertical direction
P Patient
P1 Eye
P2 Nose
P3 Nostrils
P4 Nasal cavity
P4L Nasal cavity extending direction
P5 Bone window
R1 Lacrimal gland
R2 Puncta
R3 Canaliculus
R4 Lacrimal sac
R5 Surgical area
R5S Incision area
R5L1 Longitudinal first direction of the lacrimal sac
R5L2 Longitudinal second direction of the lacrimal sac
R6 Nasolacrimal duct

The invention claimed is:

1. A lacrimal sac incision knife which is insertable into nasal cavity of patient, the lacrimal sac incision knife configured to incise the lacrimal sac located in the back of the nasal cavity, comprising:

a grip portion arranged to extend in a predetermined longitudinal direction to be held by an user of the lacrimal sac incision knife, a shank portion connected to the grip portion, the shank portion entirely linearly extending in the longitudinal direction, wherein the shank portion comprises a base portion extending in the longitudinal direction and a blade portion connected to the base portion at a front end region in the longitudinal direction, the blade portion comprises a stabbing blade provided at the front end region in the longitudinal direction and a pair of side blades having a first side blade and a second side blade, the first side blade being formed at a first side of the blade portion in the width direction and the second side blade being formed at a second side of the blade portion in the width direction, the stabbing blade defines a lacrimal sac stabbing portion which can be stabbed to the lacrimal sac in a state that the grip portion is held by the user, one of the first side blade and the second side blade defines a first lacrimal sac incision portion which incises the lacrimal sac in a first longitudinal direction of the lacrimal sac as the lacrimal sac incision knife is operated to move in a first width direction, the other of the first side blade and the second side blade defines a second lacrimal sac incision portion which incises the lacrimal sac in a second longitudinal direction of the lacrimal sac, as the state is kept such that the grip portion is held by the user and as the lacrimal sac incision knife is operated to move in a second width direction, the blade portion has a length size of approximately from 3.0 mm to 10.0 mm in the longitudinal direction, a maximum width size of approximately from 1.0 mm to 2.0 mm in the width direction, the stabbing blade has a blade length size of approximately 1.0 mm to 4.0 mm in the longitudinal direction, a maximum width size of approximately from 1.0 mm to 2.0 mm in the width direction, the first side blade and the second side blade respectively have a blade length size of approximately 2.0 mm to 6.0 mm in the longitudinal direction, wherein the base portion is arranged to comprise a taper portion such that the closer to the blade portion, the gradually thinner a thickness of the taper portion becomes in the longitudinal direction and wherein a region where the first side blade and the second side blade are formed is arranged such that a thickness of this region is constant, wherein the taper portion is arranged to have a length in the longitudinal direction as from approximately 3.0 mm to approximately 7.0 mm, and wherein the taper portion is connected with the blade portion such that the thickness of the taper portion is gradually decreased from approximately 0.3 mm to approximately 0.15 mm as gel closer to the blade portion, and wherein the region of the blade portion where the first side blade and the second side blade are formed is arranged to have a thickness of approximately 0.15 mm in the longitudinal direction.

2. The lacrimal sac incision knife as described in claim 1, wherein the base portion is arranged to have a length in the longitudinal direction approximately twice as long as the length of the blade portion.

3. The lacrimal sac incision knife as described in claim 1, wherein the shank portion is arranged to have a length in the longitudinal direction as from approximately 15.0 mm to approximately 50.0 mm, the base portion is arranged to have a length in the longitudinal direction as from approximately 5.0 mm to approximately 47.0 mm.

4. The lacrimal sac incision knife as described in claim 1, wherein a width between the first side blade and the second side blade is tapered towards the stabbing blade.

* * * * *